US009107581B2

(12) United States Patent
Gleich et al.

(10) Patent No.: US 9,107,581 B2
(45) Date of Patent: Aug. 18, 2015

(54) ELASTOGRAPHY DEVICE AND METHOD FOR DETERMINING AND IMAGING OF MECHANICAL AND ELASTIC PARAMETERS OF AN EXAMINATION OBJECT

(75) Inventors: Bernhard Gleich, Hamburg (DE); Jürgen Weizenecker, Norderstedt (DE)

(73) Assignee: Koninklijke Philips N.V., Eindhoven (NL)

( * ) Notice: Subject to any disclaimer, the term of this patent is extended or adjusted under 35 U.S.C. 154(b) by 2227 days.

(21) Appl. No.: 10/552,774

(22) PCT Filed: Apr. 15, 2004

(86) PCT No.: PCT/IB2004/050445
§ 371 (c)(1),
(2), (4) Date: Oct. 12, 2005

(87) PCT Pub. No.: WO2004/091408
PCT Pub. Date: Oct. 28, 2004

(65) Prior Publication Data
US 2006/0189868 A1 Aug. 24, 2006

(30) Foreign Application Priority Data
Apr. 15, 2003 (EP) .................................... 03101021

(51) Int. Cl.
*A61B 5/05* (2006.01)
*A61B 5/055* (2006.01)
*A61B 8/00* (2006.01)
*A61B 5/00* (2006.01)
*A61N 2/02* (2006.01)
*A61B 8/08* (2006.01)
*A61B 5/04* (2006.01)
*A61N 1/40* (2006.01)

(52) U.S. Cl.
CPC ................ *A61B 5/0048* (2013.01); *A61B 5/05* (2013.01); *A61B 5/0515* (2013.01); *A61B 8/485* (2013.01); *A61N 2/02* (2013.01); *A61B 5/04005* (2013.01); *A61B 5/055* (2013.01); *A61B 8/5223* (2013.01); *A61N 1/406* (2013.01)

(58) Field of Classification Search
CPC .... A61B 5/0048; A61B 5/0515; A61B 8/485; A61B 8/5223; A61B 8/00; A61B 5/055; A61B 5/05; A61B 5/04005

USPC .......................... 600/407, 409, 410; 607/103
See application file for complete search history.

(56) References Cited

U.S. PATENT DOCUMENTS

| 3,953,731 | A | * | 4/1976 | Forsen .......................... 250/290 |
| 4,993,416 | A | | 2/1991 | Ophir |
| 5,366,435 | A | * | 11/1994 | Jacobson ......................... 600/13 |
| 5,726,650 | A | * | 3/1998 | Yeoh et al. ....................... 341/70 |
| 6,470,220 | B1 | * | 10/2002 | Kraus et al. ................... 607/103 |
| 6,486,669 | B1 | | 11/2002 | Dargatz et al. |
| 7,439,736 | B2 | * | 10/2008 | Meaney et al. ............... 324/307 |
| 7,553,283 | B2 | * | 6/2009 | Sandrin et al. ................ 600/438 |
| 2001/0012915 | A1 | | 8/2001 | Massebgill et al. |
| 2002/0010399 | A1 | | 1/2002 | Konofagou et al. |

FOREIGN PATENT DOCUMENTS

| DE | 29722630 U1 | 7/1998 |
| DE | 197 54 085 A1 | 6/1999 |
| DE | 19754085 A1 | 10/1999 |
| DE | 19952880 A1 | 12/2000 |
| EP | 0708340 A1 | 4/1996 |

* cited by examiner

Primary Examiner — Vani Gupta

(57) ABSTRACT

The present invention relates to a device for determining mechanical, particularly elastic, parameters of an examination object, comprising a) at least one arrangement for determining the spatial distribution of magnetic particles in at least one examination area of the examination object, comprising a means for generating a magnetic field with a spatial profile of the magnetic field strength such that there is produced in at least one examination area a first part-area having a low magnetic field strength and a second part-area having a higher magnetic field strength, a means for detecting signals which depend on the magnetization in the examination object, particularly in the examination area, that is influenced by a spatial change in the particles, and a means for evaluating the signals so as to obtain information about the, in particular temporally changing, spatial distribution of the magnetic particles in the examination area; and b) at least one means for generating mechanical displacements, in particular oscillations, at least in and/or adjacent to the examination area of the examination object. The invention furthermore relates to a method for determining mechanical and/or physical parameters of an examination object, in particular using a device according to the invention. The invention further relates to magnetic particle compositions that can be used in that method according to the invention.

9 Claims, No Drawings

ELASTOGRAPHY DEVICE AND METHOD FOR DETERMINING AND IMAGING OF MECHANICAL AND ELASTIC PARAMETERS OF AN EXAMINATION OBJECT

The present invention relates to a device and method for determining and in particular imaging of mechanical, particularly elastic, parameters of an examination object. The invention further relates to magnetic particle compositions that can be used in the method according to the invention.

The determination of mechanical, in particular elastic, properties of materials and of biological tissue is highly important in order to be able to know the exact condition within such examination objects. This is because a change in the structural properties of the examination object is often also associated with a change in the elastic behavior. For example, increasing or decreasing the internal friction within an object has an effect on the elastic behavior of said object. In the same way, differences in density can be detected and used to determine the condition of materials and biological tissue for example.

Known elastography methods are used to determine mechanical parameters and for imaging using the ultrasound technique. By way of example, DE-A 197 54 085 discloses an ultrasound elastography method in which elastic tissue properties are detected in a technical manner and visualized qualitatively and quantitatively in the form of sectional images. Said method makes use of the fact that when a mechanical pressure is exerted on a section of tissue, resulting in deformation of the tissue, areas having different elastic properties deform differently. Such methods are described for example in US 2002/0010399 A1 and U.S. Pat. No. 4,993,416. US 2002/0010399 A1 essentially describes the detection of elastic parameters of preferably soft tissue. First and second ultrasound pulses are directed along the transducer axis onto the object that is to be examined and the signals that are reflected in each case are evaluated using Fourier analysis. According to U.S. Pat. No. 4,993,416, it is advantageous if a large number of ultrasound transducers are arranged radially and used sequentially for tissue examination purposes. At present, these methods cannot be used universally and generally provide informative imaging only in respect of the surface region of the examination object.

Magnetic resonance elastography (MRE) is also known for determining mechanical parameters of an examination object. In MRE methods, use is made of the fact that the phase in a magnetic resonance image of the examination object changes as a result of the mechanical oscillations active therein. The extent of this change depends on the displacement as a result of the mechanical oscillation. Using the MR phase images obtained, it is thus possible to image the phase of the nuclear magnetization, from which it is possible to derive information about specific mechanical parameters of the tissue. Conventional MRE methods, as described for example in EP-A 708 340 or in Proceeding of ISMRM 1997, page 1905, Vancouver, have the disadvantage that results suitable for evaluation can only be obtained if no reflections occur in the examination object and if only transverse oscillations propagate in the object. In order to overcome this problem, DE 199 52 880 A1 proposes an MRE method in which contribution and phase of the displacement are determined in a three-dimensional area in respect of three directions that are perpendicular to one another, and at least one mechanical parameter is calculated from these displacement values and from the spatial derivation thereof in at least part of the three-dimensional area. It is also described that it is possible to use longitudinal oscillations in the examination object for the determination of mechanical properties. In such a method, use is often made of a magnetic resonance arrangement which has already been described in DE 297 22 630 U1. However, MRE technology is complex in terms of apparatus and cost-intensive and is therefore suitable only for a limited number of applications. In additional, relatively long examination times must be taken into consideration because of the not very high signal-to-noise ratios in the MRE method.

It would therefore be desirable to be able to make use of an arrangement for determining the mechanical, in particular elastic, behavior of examination objects which does not have the disadvantages of the prior art and which is particularly simple and cost-effective to produce, can be used universally and allows short measurement times at the same time as a high resolution. In addition, it is an object of the invention to be able to determine mechanical and/or elastic properties at any location of an examination object, regardless of the distance from the surface thereof. It is furthermore an object of the invention to provide an elastography method which can be used on a wide range of examination objects and provides very precise results in a reproducible manner.

According to the invention there is provided a device that comprises a) at least one arrangement for determining the spatial distribution of magnetic particles in at least one examination area of the examination object, comprising a means for generating a magnetic field with a spatial profile of the magnetic field strength such that there is produced in at least one examination area a first part-area having a low magnetic field strength and a second part-area having a higher magnetic field strength, a means for detecting signals which depend on the magnetization in the examination object, particularly in the examination area, that is influenced by a spatial change in the particles, and a means for evaluating the signals so as to obtain information about the, in particular temporally changing, spatial distribution of the magnetic particles in the examination area; and b) at least one means for generating mechanical displacements, in particular oscillations, at least in and/or adjacent to the examination area of the examination object.

Using the device according to the invention, it is possible to trace and store the displacement and the degree of displacement of the magnetic particles out of the rest position, with a high resolution and also deeper in a body than with the known techniques. It is also possible to image pressure variations in the examination area, in particular when the magnetic particles are in air bubbles as will be described below. The device according to the invention is consequently suitable for determining the mechanical, in particular elastic, behavior of articles and bodies, in particular of tissue and organs, in areas that are close to the surface and far from the surface. It has furthermore been found that the device according to the invention is also suitable in particular for examining respiratory organs, in particular in real time.

According to the invention it may be provided that the means for generating mechanical displacements or oscillations comprises at least one oscillating element, an oscillation generator and an oscillation transmission means for transmitting oscillations from the oscillation generator to the oscillating element and/or at least one sound source, in particular an ultrasound source.

The oscillations are usually generated outside and at a distance from the magnet arrangement in the oscillation generator. Use may be made of oscillation generators known from the prior art. Suitable oscillation generators may likewise have metal elements. Oscillations can be generated, for example, by means of piezoelements, an oscillation coil or an oscillator, use preferably being made for the method according to the invention of oscillations in the range from 50 Hz to 500 Hz, in particular from 500 Hz to 250 Hz. These oscillations are usually transmitted by means of suitable oscillation transmission means to the actual oscillating element which during operation is placed on the examination object. All parts which are located in or near the magnet arrangement advantageously do not affect the gradient field and are accordingly preferably not made of metal. Hence, it is preferred that the oscillation generator is arranged outside and at a distance from the magnet arrangement and the oscillating element and the oscillation transmission means are made of non-metallic and/or metallic material.

The arrangement for determining the spatial distribution of magnetic particles may be combined with known elastography methods and with sonography methods. Suitable oscillations are accordingly surface waves which do not change the volume of the object during oscillation, as are used for example in elastography, e.g. magnetic resonance elastography, and also bulk waves which, at a given frequency, can penetrate much deeper into objects. Bulk waves are used for example in sonography. Suitable devices and instruments for generating oscillations or waves, as are used in elastography or sonography, are known to the person skilled in the art.

One expedient refinement of the device according to the invention has at least one means, in particular at least one coil arrangement, for changing the spatial position of the two part-areas in the examination area so that the magnetization of the particles changes locally.

In principle, the examination area can be scanned and examined by changing the relative spatial position of the part-area having a low magnetic field strength and of the part-area having a higher magnetic field strength. This likewise comprises an arrangement in which a magnetic field is superposed on the gradient field, in particular on the part-area having a low magnetic field strength, in order in this way to detect the change in or degree of the magnetization of the magnetic particles in the part-area having a low field strength.

Furthermore, according to another refinement account should be taken of the fact that the means for generating the magnetic field comprise a gradient coil arrangement for generating a magnetic gradient field which in the first part-area of the examination area reverses its direction and has a zero crossing.

Also suitable is a device according to the invention which has a means for generating a temporally changing magnetic field that is superposed on the magnetic gradient field, for the purpose of moving the two part-areas in the examination area.

A suitable device according to the invention is characterized by a coil arrangement for receiving signals induced by the temporal change in the magnetization in the examination area.

According to a further embodiment, the device according to the invention has means for generating a first and at least a second magnetic field that are superposed on the magnetic gradient field, where the first magnetic field changes slowly in time terms and with a high amplitude and the second magnetic field changes rapidly in time terms and with a low amplitude.

A further refinement of the device according to the invention provides that the two magnetic fields run essentially perpendicular to one another in the examination area.

A spatially inhomogeneous magnetic field is generated in the examination area by means of the arrangement used according to the invention. In the first part-area the magnetic field is so weak that the magnetization of the particles differs to a greater or lesser extent from the external magnetic field, that is to say is not saturated. This first part-area is preferably a spatially coherent area; it may be a punctiform area or else a line or a flat area. In the second part-area (i.e. in the rest of the examination area outside the first part) the magnetic field is strong enough to keep the particles in a state of saturation. The magnetization is saturated when the magnetization of virtually all particles is aligned in approximately the direction of the external magnetic field, so that the magnetization there increases much less with a further increase in the magnetic field than in the first part-area given a corresponding increase in the magnetic field. By changing the position of the two part-areas within the examination area, the (overall) magnetization in the examination area changes. If, therefore, the magnetization in the examination area or physical parameters influenced thereby is/are measured, information about the spatial distribution of the magnetic particles in the examination area can then be derived therefrom. In order to change the spatial position of the two part-areas in the examination area, for example, a magnetic field that can be changed locally and/or temporally can be generated. It may also be provided that the signals induced in at least one coil by the temporal change in the magnetization in the examination area are received and evaluated in order to obtain information about the spatial distribution of the magnetic particles in the examination area. Signals that are as high as possible can be obtained by the spatial position of the two part-areas changing as rapidly as possible. A coil which is used to generate a magnetic field in the examination area can be used to detect the signals. However, at least one special coil is preferably used.

The change in the spatial position of the part-areas may also take place, for example, by means of a magnetic field that can be changed temporally. In this case a likewise periodic signal is induced in a coil. However, this signal may be difficult to receive since the signals generated in the examination area and the temporally changing magnetic field are active at the same time; it is therefore not readily possible to distinguish between the signals induced by the magnetic field and the signals induced by changing the magnetization in the examination area. However, this can be avoided by a temporally changing magnetic field acting on the examination area in a first frequency band and, from the signal received in the coil, a second frequency band which contains higher frequency components than the first frequency band being evaluated so as to obtain information about the spatial distribution of the magnetic particles. This makes use of the fact that the frequency components of the second frequency band can occur only by virtue of a change in the magnetization in the examination area as a result of the non-linearity of the magnetization characteristic. If the temporally changing magnetic field has a sinusoidal periodic profile, the first frequency band consists only of a single frequency component—the sinusoidal fundamental component. By contrast, besides this fundamental component the second frequency band also contains higher harmonics (so-called upper harmonics) of the sinusoidal fundamental component, which can be used for the evaluation.

In a preferred arrangement for the device according to the invention the means for generating the magnetic field comprise a gradient coil arrangement for generating a magnetic gradient field which in the first part-area of the examination area reverses its direction and has a zero crossing. This magnetic field is—if the gradient coil arrangement comprises e.g. two identical windings which are arranged on either side of the examination area but which are flowed through by opposite currents (Maxwell coil)—zero at a point on the winding axis and increases virtually linearly on either side of this point with opposite polarity. Only in the case of particles which are located in the region around this field zero point is the magnetization not saturated. In respect of particles outside this area the magnetization is in a state of saturation.

An arrangement may be provided with means for generating a temporally changing magnetic field that is superposed on the magnetic gradient field for the purpose of moving the two part-areas in the examination area. The area generated by the gradient coil arrangement is in this case moved around the field zero point, i.e. the first part-area, within the examination area by the temporally changing magnetic field. Given a suitable temporal profile and orientation of this magnetic field it is possible in this way for the field zero point to pass through the entire examination area.

The change in magnetization that is associated with the movement of the field zero point may be received by means of an appropriate coil arrangement. The coil used to receive the signals generated in the examination area may be a coil which is already used to generate the magnetic field in the examination area. However, there are also advantages to using a special coil for receiving, since this can be decoupled from the coil arrangement that generates a temporally changing magnetic field. Moreover, an improved signal-to-noise ratio can be achieved with one coil - but all the more so with a number of coils.

The amplitude of the signals induced in the coil arrangement is higher the quicker the position of the field zero point in the examination area changes, that is to say the quicker the temporally changing magnetic field superposed on the magnetic gradient field changes. However, it is technically difficult to generate on the one hand a temporally changing magnetic field whose amplitude is sufficient to move the field zero point to the point of the examination area and whose rate of change is sufficiently high to generate signals having a sufficient amplitude. Particularly suitable for this are those arrangements which have means for generating a first and at least a second magnetic field that are superposed on the magnetic gradient field, where the first magnetic field changes slowly in time terms and with a high amplitude and the second magnetic field changes rapidly in time terms and with a low amplitude. Two magnetic fields which change at different rates and with different amplitudes are generated—preferably by two coil arrangements. A further advantage is that the field changes may be so fast (e.g. >20 kHz) that they are above the limit of human audibility. It may likewise be provided that the two magnetic fields run essentially perpendicular to one another in the examination area. This allows the movement of the field-free point in a two-dimensional area. An expansion to a three-dimensional area is obtained by virtue of a further magnetic field which has a component that runs perpendicular to the two magnetic fields. An arrangement having a filter connected downstream of the coil arrangement is likewise advantageous, said filter suppressing from the signal induced in the coil arrangement the signal components in a first frequency band and allowing through the signal components in a second frequency band which contains higher frequency components than the first frequency component. This makes use of the fact that the magnetization characteristic in the region in which the magnetization passes from the unsaturated state to the saturated state is non-linear. This non-linearity means that a magnetic field which runs for example in a sinusoidal manner over time with the frequency f in the range of non-linearity, brings about a temporally changing induction with the frequency f (fundamental component) and integer multiples of the frequency f (upper or higher harmonics). The evaluation of the upper harmonics has the advantage that the fundamental component of the magnetic field that is active at the same time for moving the field-free point does not have any influence on the evaluation.

According to a further aspect of the present invention there is provided a method for determining mechanical and/or physical parameters of an examination object comprising the introduction of magnetic particles into at least part of an examination area of the examination object, the generation of at least one mechanical displacement, in particular mechanical oscillations, in at least the examination area of the examination object, the generation of a magnetic field with a spatial profile of the magnetic field strength such that there is produced in the examination area a first part-area having a low magnetic field strength and a second part-area having a higher magnetic field strength, the changing of the spatial position of the two part-areas in the examination area so that the magnetization of the particles changes locally, the detection of signals which depend on the magnetization in the examination area that is influenced by this change, the evaluation of the signals so as to obtain information about the, in particular temporally changing, spatial distribution of the magnetic particles in the examination area, and the comparison of the information obtained about the spatial distribution of the magnetic particles so as to determine elastic parameters, in particular of states of different mechanical stress.

In one preferred embodiment of the method according to the invention it is provided that the magnetic particles in the examination area are present at and/or on the surface of gas bubbles and/or drops of liquid. Particularly advantageous results in terms of resolution, sensitivity and measurement accuracy can be obtained when using such air or gas bubbles in the examination area, on which bubbles there are magnetic particles. On account of surface phenomena, magnetic particles often gather spontaneously on the surface of these gas bubbles. However, it is likewise possible to introduce gas bubbles and magnetic particles at the same time or almost at the same time into the examination object.

The gas bubbles deform under the influence of a displacement or a pressure wave causing minor changes in the distance between the magnetic particles at the interface between the gas bubble and the surrounding medium resulting in a different response to the external magnetic field. At a position near to the position of the field free point where the magnetic particles are close to saturation, the magnetic bubbles are very sensitive to pressure or displacement variations. These so-called magnetic bubbles are quasi wide response microphones which may be present in the examination area in a more or less uniformly distributed manner. These magnetic bubbles are particularly suitable at high oscillation frequencies, for example in the region of 50 kHz, particularly 100 kHz up to 20 MHz, and provide a very high resolution. A further advantage, particularly when using the above-described so-called magnetic bubbles, is that during the examination of the part-area having a low magnetic field strength there is no need for excitation by means of an external magnetic field, since the change in magnetization can already be detected by means of the oscillations, e.g. via a sound field. This applies in particular to the use of high frequency sound waves. If, for example, the gradient field at one location has a magnitude which lies close to the magnitude for reaching saturation, the oscillation of the magnetic bubbles can bring about a change in the magnetization. There is thus, in particular close to the field zero point of the gradient field, a location which reacts sensitively to fluctuations in pressure and converts these fluctuations into an external magnetic field. In measurement terms, this has the advantage that there is no strong background of the excitation frequency during detection of this magnetic field. Instead of moving the relative position of the part-areas having a low magnetic field strength and a higher magnetic field strength with respect to one another by means of a coil or transmitter unit, in the embodiment shown only the object and the field zero point need be moved relative to one another. In this variant of the method there is, at least to a first approximation, a deviation of the direction of the pressure of the wave field at one location Particularly when using magnetic particles gathered on gas bubbles or drops of liquid, it should be noted that an inhomogeneous distribution of these bubbles or drops in the examination area may lead to a variation in sensitivity. However, this inhomogeneous distribution can be measured by the above-described magnetic imaging method, resulting in a first calibration. Nevertheless, during the method according to the invention, particularly when using very high oscillation frequencies, individual bubbles may also be destroyed on account of the associated high pressure or simply loose gas volume over time, for example by the dissolving of the gas in the surrounding medium. If there is a restriction to carrying out a calibration, as described above, via the determination of the distribution of the magnetic particles, this may possibly lead to false information. It has proved advantageous to apply a known change in pressure to the examination area and to compare the response signals obtained with those obtained upon again subjecting it to this known change in pressure. The applied pressure fluctuations are preferably low frequency and are most advantageously applied to the examination area or examination object uniformly from all sides. By way of example, pressure fluctuations of the ambient air pressure, preferably below the audible threshold of about 16 Hz, are suitable for such a calibration. This subjecting of the examination area to a known change in pressure may be carried out both separately from the measurement method according to the invention and during the actual measurement method, for example periodically. In this case, a low frequency oscillation is superposed on the actual measurement frequency for calibration purposes.

When producing oscillations at low frequencies, for example in the region of 10 kHz, particularly 1 kHz and below, the elastic properties of the examination area can also be determined particularly well with magnetic particles present in a distributed manner in this area, without the latter having to be present on gas bubbles. Lower frequencies have the advantage that objects that are deeper in the examination area, for example organs deeper in the body, can be examined.

In one embodiment of the method according to the invention, use is made of magnetic particles that are anisotropic, preferably having an internal anisotropy field of at least 0.1 mT. The method comprises the steps of 1) introducing anisotropic particles into the examination area, 2) create orientation of the particles in a zone near the field free zone, 3) move the field free zone to measure the response field of the magnetic particles, 4) switch on the sound wave or displacement and 5) move the field free zone to measure the response field of the oriented magnetic particles in a new position as a result of said sound wave or displacement. This is particularly useful, when there is no suitabe contrast by e.g. an inhomogeneous distribution of the particles in a tissue. By this method an artificial contrast can be created by aligning the magnetic particles in a inhomogeneous way.

With the method according to the invention it is possible to visualise the a acoustic waves in the examination area. If an elastic in homogeneity is present in the examination area the acoustic waves are disturbed. From the deconvolution of the acoustic waves an image can be created of the object in which the contrast relates to the differences in the elastic properties in the examination area. This method can be applied for example for detecting tumours, in particular breast tumour. Tumours can be visualised with this method because they typically have a higher modulus of elasticity that the surrounding tissue. With proper calibration the elastic tensor or modulus can be determined. Because the required scan speed for measuring a displacement factor or an elastic tensor is very high, preferably a small part of the examination area is scanned at this very high speed. For imaging, the full area of the examination area is scanned by consecutive imaging adjacent said small volumes.

One further development of the method according to the invention is characterized in that a temporally changing magnetic field acts on the examination area in a first frequency band and, from the signal received in the coil, a second frequency band which preferably contains higher frequency components than the first frequency band is evaluated so as to obtain information about the spatial distribution of the magnetic particles.

According to the invention it is provided that the magnetic particles become saturated upon application of an external magnetic field, in particular having a strength of about 100 mT or less. Of course, higher saturation field strengths are also suitable for the method according to the invention.

For many applications, suitable magnetic field strengths are even about 10 mT or less. This strength is sufficient even for many tissue or organ examinations. However, good measurement results can also be achieved with field strengths in the region of 1 mT or less or of around 0.1 mT or less. By way of example, concentration, temperature, pressure or pH can be determined with a high degree of accuracy and definition at magnetic field strengths of around 10 mT or less, of around 1 mT or less and at around 0.1 mT or less.

Within the context of the present invention, the term external magnetic field in which the magnetic particles become saturated or are saturated is to be understood as meaning a magnetic field in which around half the saturation magnetization is achieved.

Suitable magnetic particles are those which can become saturated in the case of a sufficiently small magnetic field. A necessary prerequisite for this is that the magnetic particles have a minimum size or a minimum dipole moment. Within the context of the present invention, the term magnetic particles consequently also encompasses magnetizable particles.

Suitable magnetic particles advantageously have dimensions which are small compared to the size of the voxels, the magnetization of which is to be determined by means of the method according to the invention. Furthermore, the magnetization of the particles should preferably become saturated at field strengths of the magnetic field which are as low as possible. The lower the field strength necessary for this, the higher the spatial resolution capability and the weaker the (external) magnetic field that is to be generated in the examination area. Moreover, the magnetic particles should have a dipole moment that is as high as possible and a high saturation induction in order that the change in magnetization results in output signals that are as high as possible. When using the method for medical examinations, it is also important that the particles are non-toxic.

According to a preferred refinement of the method according to the invention it is proposed that the magnetic particle is a monodomain particle the magnetization of which can be reversed by means of Neel's rotation and/or by means of Brown's rotation.

Suitable magnetic monodomain particles are preferably dimensioned such that only a single magnetic domain (the monodomain) can form therein and white regions are not present. According to a particularly preferred variant of the invention, suitable particle sizes lie in the range from 20 nm to around 800 nm, with the upper limit also depending on the material used. In respect of monodomain particles, use is preferably made of magnetite ($Fe_3O_4$), maghemite ($\gamma$-$Fe_2O_3$) and/or non-stoichiometric magnetic iron oxides.

In general it is advantageous, particularly if a rapid reversal of the magnetization based on Neel's rotation is desired, that the monodomain particles have a low effective anisotropy. The term effective anisotropy is in this case to be understood as meaning the anisotropy resulting from the form anisotropy and the crystal anisotropy. In the aforementioned case, a change in the magnetization direction does not require any rotation of the particles. Alternatively, monodomain particles having a high effective anisotropy can be used if it is desired that the magnetization reversal upon application of an external magnetic field takes place by means of Brown's rotation or geometric rotation.

According to an alternative embodiment of the method according to the invention it may be provided that the magnetic particle is a hard- or soft-magnetic multidomain particle. These multidomain particles are usually relatively large magnetic particles in which it is possible for a number of magnetic domains to form. Such multidomain particles advantageously have a low saturation induction.

Hard-magnetic multidomain particles essentially have the same magnetic properties as monodomain particles having a high effective anisotropy. Soft-magnetic multidomain particles with a low saturation magnetization have the advantage that they may be shaped in any way in order to be able to be used in the method according to the invention. If they have an asymmetric external shape, they are also particularly suitable for local viscosity measurements in the examination area. Soft-magnetic multidomain particles with a high saturation magnetization are advantageously to be configured such that the demagnetization factor is small. Both symmetric and asymmetric shapes can be used. For example, a soft-magnetic active substance with a high saturation magnetization may be applied as a thin coating to a sphere or cube which itself cannot be magnetized.

The method according to the invention is in particular also suitable for determining, in particular locally, the internal pressure, the change in internal pressure, the volume and/or the change in volume of gas bubbles present in the examination area of the examination object.

Moreover, the method according to the invention is suitable for determining, in particular locally, the temperature, the change in temperature, the rigidity, the change in rigidity, the density and/or the change in density, the pressure, the displacement, the modulus of elasticity and/or the shear modulus in the examination area of the examination object.

According to the invention it may be provided that the mechanical parameters are detected continuously or at intervals.

The present invention was based on the surprising knowledge that mechanical properties, in particular elastic properties, and density information for locally delimited areas within examination objects can readily be determined in a reproducible manner. Conclusions can also be drawn about the internal pressure of gas bubbles in an examination object. In particular, the arrangement according to the invention can no longer be used just to examine only the area of objects that lies close to the surface, but now also to be able to obtain information about the mechanical and elastic condition inside bodies. The device according to the invention thus allows, in a simple and reliable manner, the local determination of parameters such as temperature, rigidity, internal gas pressure, gas volume and density and also the tracing and determination of the change in these parameters, in particular also in real time. Furthermore, the determination of the pH is also possible.

Using the device according to the invention, it is thus possible to assign mechanical and elastic properties also to narrowly delimited locations within objects, with a very high resolution. Compared to conventional elastography methods, an extremely high signal-to-noise ratio is obtained, resulting in much shorter measurement times without losses having to be taken into account in terms of the quality of the measurements. Furthermore, all elastic parameters of the elasticity tensor can be determined. In addition, a very reliable measurement result is always obtained since low frequency oscillations may be superposed on the actual measurement for calibration purposes.

It is also advantageous that the magnetic particles do not necessarily have to be distributed homogeneously over the examination area in order to be able to obtain the desired information about said area. Rather, deformation either of the examination area or of the magnetic bubbles on account of oscillations can be detected and evaluated even if there is an inhomogeneous distribution of said particles. In the case of a homogenous distribution of the particles in the examination area, it has proven advantageous to use those magnetic particles the magnetization of which can be reversed by means of both Neel's rotation and Brown's rotation. In this case, the different time dependence of the magnetization reversal by means of Neel's rotation or Brown's rotation can be used to obtain information about the local elastic behavior of the examination object in the examination area. By way of example, in the case of an inhomogeneous particle distribution, e.g. if part-areas of the examination area do not have any magnetic particles, characteristic variables for these areas that do not have any magnetic particles can also be determined indirectly by extrapolation of the recorded signals. This may be used, for example, when air bubbles with magnetic particles on their surface are passed into the veins, from which they cannot pass into other tissue on account of their size. Information can then nevertheless also be obtained about the elastic behavior of areas beside or between these veins, which areas do not have any magnetic particles.

Besides the examination of tissue structures or organs in living things, the device according to the invention and the method according to the invention are also suitable for example for examining rubber materials and components, as are used increasingly in plastics technology. The internal elastic properties of rubber components, tires or components based on thermoplastic elastomers can be examined with a high resolution and reliably using the method according to the invention, with elastic parameters being obtained at each location of the examination area.

The invention further relates to magnetic particle compositions that can be used in the method according to the invention to enhance contrast and resolution. The magnetic particle compositions according to the invention make use of the effect that magnetic particles, when they are very close together, are under the influence of each other's magnetic fields. Because of the coupling with the magnetic fields of the neighbouring particles, the response of the individual particles to an external magnetic fields is changed. The distance between the particles can for example be changed by a displacement in the surrounding medium, for example brought about by the acoustic waves. The change in distance and the concomitant change in magnetic properties result in a different response to the applied external magnetic field in the magnetic particle imaging method. The different response is used to produce a contrast in the image. The distance required to get a change in magnetic behaviour between a first and a second state on separation or agglomeration of the particles depends on nature of the magnetic particles. Preferably, the distance between the particles is less than 10 times, preferably less than 8 and more preferably less than 5 times the diameter of the magnetic particles. With distance the core to core distance is meant. As it is very difficult to move the particles from each other when they are too close, the distance preferably is at least 3 times, preferably at least 4 times the average particle diameter.

One embodiment of such a magnetic particle composition is a magnetic gas bubble composition, comprising one or more gas bubbles in a liquid medium wherein magnetic particles are present at the interface of the gas bubble and the liquid medium.

The average particle to particle distance between the magnetic particles at the interface between the gas bubble and the liquid medium is preferably between 3 and 10 times the average diameter of the magnetic particles and is preferably less than 8, more preferably less than 5 times the magnetic particle size. The magnetic gas bubble composition may comprise a surfactant for localising the magnetic particles substantially at the interface between the gas bubble and the liquid medium. Preferably, the magnetic particles are attached to a surfactant molecule. The size of the magnetic gas bubble can in principle vary in a wide range. In a preferred use of the magnetic particle imaging method, for examining living organisms, the diameter of the gas bubble is preferably between one and 10 µmeters. Preferably, the magnetic gas bubble comprise a gas having a low water solubility, in particular wherein the gas does not substantially dissolve and/or does not rapidly dissolve in water. A suitable not dissolvable gas for in the body applications is a perfluorated gas.

Magnetic gas bubble composition is can be made in different ways. One way is to introduce gas bubbles in a liquid medium. A disadvantage of liquid magnetic gas bubble composition is that the storage stability is relatively low and they are relatively difficult to make. According to another aspect of the invention there is provided a magnetic gas bubble precursor for the manufacture of a magnetic gas bubble composition wherein the gas bubble precursor comprises a shell encompassing a gas volume and wherein the shell comprises magnetic particles. The magnetic dry gas bubble precursor can be used in the dry state, but are preferably used for the manufacture of a magnetic gas bubble composition as described above, for example by dissolving a dry magnetic gas bubble precursor in a suitable liquid medium. The advantage of this try magnetic gas bubble precursor is that it can be stored with a relatively long shelflife.

The magnetic gas bubble precursor can be administered to the examination area directly in case the examination area contains a liquid medium. The magnetic gas bubble precursor can also be administered after dispersing in a liquid medium. The shell material may at least partly dissolve or reduce viscosity in contact with the liquid medium such that the magnetic particles gain freedom for rotational movement when dispersed in the liquid medium. The shell material can for example be a material that dissolves in an aqueous medium like blood, for example a polysaccharide, a starch or a low viscosity hydrophilic polymer material. The shell material can also be a material that melts or reduces viscosity at the temperature prevailing in the examination area or a material that degrades or decompose to a low viscosity in conditions prevailing in the examination area.

The bubble may comprise a drug. The drug may be transported to a specific area in the examination fields in a controlled manner controlled by the imaging technique, and locally released by destroying the gas bubble, for example by using the magnetostriction effect or by irradiation was electromagnetic radiation or by acoustic waves.

In an alternative embodiment of the invention there is provided a magnetic particle composition comprising two or more magnetic particles wherein the average particle to particle distance between the magnetic particles is between 3 and 10 times the average particle diameter and wherein the particles are agglomerated and/or coupled-together in a spatially delimited way by embedding in a viscous elastic medium. The viscous elastic medium is chosen such that the distance between the particles varies as response to displacement caused by acoustic waves.

In general the magnetic particles in the magnetic particle composition, are chosen such that good magnetic particle images, in particular a good resolution can be obtained in a given field gradient. In unpublished German patent application number 101 51778.5 a magnetic particle imaging method is described. It is generally described that magnetic monodomain particles having a size between 20 and 800 nanometres or a glass beat coated with a magnetic coating can be used in this method. However, in order to achieve a good magnetic imaging contrast and resolution at relatively low magnetic field gradients, improved magnetic particle compositions are highly desirable. The inventors have found magnetic particles having improved magnetic particle imaging properties.

Preferably, the magnetic particles in the magnetic particle composition have a magnetization curve having a step change, the step change being characterized in that the magnetization change, as measured in an aqueous suspension, in a first field strength window of magnitude delta around the inflection point of said step change is at least a factor 3 higher than the magnetization change in the field strength windows of magnitude delta below or in the field strength windows of magnitude delta above the first field strength window, wherein delta is less than 2000 microtesla, preferably less than 1000 microtesla, and wherein the time in which the magnetisation step change is completed in the first delta window is less than 0.01 seconds, preferably less than 0.005 sec, more preferably less than 0.001, most preferably less than 0.0005 seconds. It has been found, that such magnetic particles are particularly suitable for magnetic particle imaging, in particular for obtaining a good resolution of the image. It is further preferred, that the magnetic particle composition has a magnetisation curve, wherein the step change is at least 10%, preferably at least 20%, more preferably at least 30% and most preferably at least 50% of the total magnetisation of the particle composition as measured at an external magnetisation field of 1 Tesla. It is further preferred, that the magnetization change in the first field strength window of magnitude delta around the inflection point of said step change is at least a factor 4, preferably at least a factor 5 higher than the magnetization change in the field strength windows of magnitude delta below or in the field strength windows of magnitude delta above the first field strength window.

The magnetic particle composition is particularly useful for use in a magnetic particle imaging technique. The particles show good spatial resolution at relatively low field strength gradients. Further, the magnetic particle composition allows for a relatively high scanning speed for examining a large examination area. For example, for application in medical magnetic particle imaging, where the step change occurs preferably at a delta value below 1000 microTesla, the particle composition has a resolution value better than between 0.1 and 10 mm at magnetic field strength gradients between 10 and 0.1 T/m. With the magnetic particle imaging technique using the magnetic particle compositions according to the invention extremely good resolution can be obtained, for example in a range from 0.1 to 10 micrometres in applications, where are very high magnetic field is gradients can be achieved, for example in microscopy.

It is preferred that the magnetic particle composition showing the required step change as described above is used in the method and all the magnetic particle compositions according to the invention.

It is noted that strictly speaking, magnetic field strength is expressed in H (A/m). However, in the present application, when reference is made to magnetic field strength, B-fields are meant. A magnetic fields B of 2000 µT as described above corresponds to an H field of 2 mT/$\mu_0$=1.6 kA/m, that is the equivalent H field that would produce a B field of 2 mT in vacuum.

A method for measuring the magnetisation curve and the required step change is as follows. A sample of a magnetic particle composition is suspended in water, optionally with the help of a simple detergent. To prevent clumping and/or to de-agglomerate the magnetic particles an ultrasound treatment possible can be used. The concentration of the magnetic particle composition is less than 0.01 gr core mass per liter of solvent. With core mass is meant the mass of the magnetic material in the magnetic particle composition. The suspension is brought into a fast magnetometer. (i.e. a device that measures the magnetization of the sample while an external field is applied). Suitable fast magnetometers are known to the expert. The magnetometer is equipped with means allowing to produce an external field at the sample position in at least two orthogonal directions simultaneously, i.e. to produce any magnetic field below a given maximum amplitude and a given maximum speed of change. The magnetisation is measured also in at least two orthogonal directions in the same plane.

First the saturation magnetisation is measured. For this, a magnetic field of about one Tesla is applied in one direction and the magnitude of magnetization is measured after at least 10 seconds. Then the measurement sequences for determining the step change starts. The sequence starts with choosing a field vector with an external field magnitude below 20 mT. This field is applied for at most 100 seconds. Then a second direction is chosen. This direction defines the scalar values of the field H and the magnetization M. The field is rapidly changed, preferably less than 1 millisecond, so that it lies now in –H direction with some magnitude below 20 mT. Then the field is changed from –H to +H e.g. in a linear way and the (now scalar i.e. projected) magnetization is recorded. The magnetization curve is recorded in less than 0.01 s but longer than 1 µs. Where the magnetisation curve shows a step change, a first window of size delta is positioned centrally on the inflection point of the magnetisation step change. Similarly, a window of size delta is positioned below and above the first window, and the required step change is evaluated by determining the change in magnetisation in each of the windows.

Whether or not a given magnetic particle composition has the required step change depends in a complicated way on many variables, for example of the size of the particles, the particle size distribution, the shape of the particles, the damping constant for Neel rotation, the type of magnetic material, the crystallinity and the stochiometry of the composition of the magnetic material. It has been found that it is particularly important that the particle size distribution of the particle composition is narrow. Preferably, the magnetic particle composition according to the invention has a narrow particle size distribution wherein at least 50 weight % of the particles have a particle size between plus or minus 50%, preferably 25%, more preferably 10% of the average particle size. Preferably, the amount of particles within the specified windows, is at least 70 wt %, preferably at least 80 wt %, and most preferably at least 90 wt %. Particularly good imaging results are obtained with mono-domain particles have a low magnetic anisotropy with a field needed for inducing Neel rotation of substantially below 10 mT, preferably below 5 mT, more preferably below 2 mT. Preferably, the magnetic particles are mono-domain particles having an average particle size between 20 and 80 nanometres, more preferably between 25 and 70 nanometres, must preferably between 30 and 60 nanometres, wherein at least 50, preferably at least 60, more preferably at least 70 weight % of the particles have a particle size between the average particle size plus or minus 10 nanometre.

In an alternative embodiment of the magnetic particle composition according to the invention, the magnetic particle is a multi-domain particle having substantially a needle shape having a demagnetisation factor of less than 0.001. This magnetic particle composition is particularly useful in non-medical applications where the needles shape is not a disadvantage. In another alternative embodiment, the magnetic particle composition according to the invention comprises magnetic particles comprising a non-magnetic core covered with a magnetic coating material, wherein the thickness of the coating is between 5 and 80 nanometres and wherein the demagnetisation factor is less than 0.01 and a diameter below 300 µm. Also in these alternative embodiments it is advantageous to have a small particle size distribution as described above. The physical parameters of the magnetic particles in these embodiments are preferably chosen to meet the step change requirement as described above for achieving good imaging properties.

The magnetic particle composition according to the invention can be manufactured by first forming magnetic particles, for example by precipitation, for example by contacting a solution comprising ferrous and ferric ions with a solution comprising sodium hydroxide as described above. In principle, a known precipitation process can be used. It is also possible to grind the particles from bulk material, for example using a high speed ball mill. The essential next step for obtaining a good magnetic particle composition is the selection and separation of the particles. The first step is to perform a size selection process by filtering and/or centrifuge methods. The next step is to perform a selection process based on the magnetic properties of the particles, for example using oscillating magnetic gradient fields.

The features of the invention that are disclosed in the above description and the claims may be essential for the implementation of the invention in its various embodiments both individually and in any desired combination.

The invention claimed is:

1. A device for determining elastic parameters of an examination object, the device comprising:
    an apparatus configured to determine the spatial distribution of magnetic particles in at least one examination area of the examination object, the apparatus comprising: a first coil configured to generate a magnetic field with a spatial profile of the magnetic field strength, wherein, in at least one examination area, a first part-area having a low magnetic field strength is produced and a second part-area having a higher magnetic field strength is produced; a second coil configured to detect signals that depend on the magnetization in the examination object, which is influenced by a spatial change in the particles; and a oscillation generator configured to produce mechanical oscillations at least in and/or adjacent to the examination area of the examination object.

2. A device as claimed in claim 1, further comprising at least a third coil configured to change the spatial position of the two part-areas in the examination area so that the magnetization of the particles changes locally.

3. A device as claimed in claim 1, wherein the oscillation generator is configured to provide oscillations to an oscillating element and/or at least one sound source.

4. A device as claimed in claim 3, wherein the oscillation generator is arranged outside and at a distance from the magnet arrangement and the oscillating element.

5. A device as claimed in claim 1, wherein the first coil comprises a gradient coil configured to generate a magnetic gradient field, which in the first part-area of the examination area reverses its direction and has a zero crossing.

6. A device as claimed in claim 1, further comprising a fourth coil configured to generate a temporally changing magnetic field that is superposed on the magnetic gradient field.

7. A device as claimed in claim 1, further comprising a fifth coil configured to receive signals induced by the temporal change in the magnetization in the examination area.

8. A device as claimed in claim 1, further comprising a sixth coil configured to generate a first and at least a second magnetic field that are superposed on the magnetic gradient field, wherein the first magnetic field changes slowly in time terms and with a high amplitude and the second magnetic field changes rapidly in time terms and with a low amplitude.

9. A device as claimed in claim 8, wherein the two magnetic fields run essentially perpendicular to one another in the examination area.

* * * * *